(12) United States Patent
Choi et al.

(10) Patent No.: US 7,892,190 B2
(45) Date of Patent: Feb. 22, 2011

(54) CHAIN STABILIZING DEVICE IN HYPERTHERMO-THERAPEUTIC APPARATUS AND METHOD OF USING THE SAME

(75) Inventors: Byung Won Choi, Chunsan-si (KR); Hyun Sik Chung, Pyungtaek-si (KR); Keun young Paek, Kimje-si (KR)

(73) Assignee: Ceragem Co., Ltd., Chunan-Si (KR)

( * ) Notice: Subject to any disclaimer, the term of this patent is extended or adjusted under 35 U.S.C. 154(b) by 1085 days.

(21) Appl. No.: 11/566,877

(22) Filed: Dec. 5, 2006

(65) Prior Publication Data
US 2007/0249443 A1 Oct. 25, 2007

(30) Foreign Application Priority Data
Apr. 11, 2006 (KR) ...................... 10-2006-0032906

(51) Int. Cl.
*A61H 15/02* (2006.01)
(52) U.S. Cl. ........................... 601/19; 601/99; 601/102; 601/103; 601/116
(58) Field of Classification Search .................... 601/15, 601/16, 18, 19, 97–103, 116, 128; 198/837, 198/841
See application file for complete search history.

(56) References Cited
U.S. PATENT DOCUMENTS
6,643,551 B1 * 11/2003 Park .......................... 607/100

2003/0196373 A1 * 10/2003 Ellis .......................... 47/1.01 P
2004/0082983 A1 * 4/2004 Park ............................ 607/96

FOREIGN PATENT DOCUMENTS
KR 20-0298656 12/2002
KR 2003-0024611 3/2003

OTHER PUBLICATIONS

English Language Abstract of KR 20-0298656. Dec. 26, 2002.
English Language Abstract of Kr 2003-0024611. Mar. 26, 2003.
U.S. Appl. No. 11/566,918 to Choi et al, filed Dec. 5, 2006.

* cited by examiner

*Primary Examiner*—Danton DeMille
(74) *Attorney, Agent, or Firm*—Greenblum & Bernstein P.L.C.

(57) ABSTRACT

The present invention is to provide a chain stabilizing device which can fundamentally solve the phenomenon of extension of a chain during use of a hyperthermo-therapeutic apparatus and allow use of existing curved rails conforming to the shape of a user's body. The present invention is to provide an apparatus for stabilizing a chain in a hyperthermo-therapeutic apparatus, comprising a chain stabilization control unit for stably moving the chain at a constant level regardless of an upward/downward movement of a hyperthermo-therapeutic unit of the hyperthermo-therapeutic apparatus during forward/backward reciprocation of the hyperthermo-therapeutic unit; and a chain-tension control unit for adjusting a tension on the chain, which can be generated during the forward and backward reciprocation of the hyperthermo-therapeutic unit.

6 Claims, 4 Drawing Sheets

CHAIN STABILIZING DEVICE IN HYPERTHERMO-THERAPEUTIC APPARATUS AND METHOD OF USING THE SAME

TECHNICAL FIELD

The present invention relates to a chain stabilizing device in a hyperthermo-therapeutic apparatus and a method of using the same, and more particularly, to a chain stabilizing device which can prevent a chain from being sagged even while a hyperthermo-therapeutic unit of a hyperthermo-therapeutic apparatus is moved in a vertical direction upon use of the hyperthermo-therapeutic apparatus, and a method of using the chain stabilizing device.

BACKGROUND ART

A hyperthermo-therapeutic apparatus that is commonly used in these days is used as a kind of physical therapeutic equipment in which a hyperthermo-therapeutic unit is reciprocated over user's vertebral regions including cervical and lumbar vertebrae to perform a hot compress as well as acupressure and simultaneously radiate far infrared rays. It is well known that such a hyperthermo-therapeutic apparatus provides a user with a treatment effect in an alternative medical treatment manner. A bed type hyperthermo-therapeutic apparatus, which performs a hyperthermo-therapeutic treatment for user's vertebral regions including cervical and lumbar vertebrae in a state where the user lies on a mat mounted on a bed-shaped frame body, is mainly used.

The bed type hyperthermo-therapeutic apparatus comprises a hyperthermo-therapeutic unit for performing a hot acupressure treatment and radiating far infrared rays on the user's vertebral regions; a movable body that is coupled to and securely supports the hyperthermo-therapeutic unit and is reciprocated in a mat; a moving means coupled to the movable body in a longitudinal direction; and a motor for generating a force causing the moving means to reciprocate the movable body in the mat. The movable body is coupled, through rollers provided at both side surfaces thereof, to rails installed at both sides of an inside portion of the mat.

However, as the function of the bed type hyperthermo-therapeutic apparatus is gradually diversified, the bed type hyperthermo-therapeutic apparatus employs curved rails similar to human's vertebral regions. In this process, there is a phenomenon in which a chain or a timing belt for use in moving the movable body is gradually extended. When the feeding motor pulls the movable body, the movable body should ascend along the curved rails, so that it is subjected to a user's load pressing down the movable body. Thus, the feeding motor should pull the movable body with a greater force. This causes a greater tension to be exerted on the chain or timing belt.

This phenomenon is a cause of a user's complaint that is more frequently made as the hyperthermo-therapeutic apparatus is utilized for a long time. In order to solve the problem, a manufacturer or the user exerts every effort to make post-management of the product.

DISCLOSURE OF INVENTION

Technical Problem

As described above, when a user continues to utilize a conventional bed type hyperthermo-therapeutic apparatus, a chain should be moved upward/downward according to the levels of curved rails. Thus, it is impossible to solve a phenomenon of extension of the chain, which inevitably occurs during use of the hyperthermo-therapeutic apparatus.

Accordingly, an object of the present invention is to provide a chain stabilizing device which can fundamentally solve the phenomenon of extension of a chain during use of a hyperthermo-therapeutic apparatus and allow use of existing curved rails conforming to the shape of a user's body.

Another object of the present invention is to provide a chain stabilizing device which can fundamentally solve the phenomenon of extension of a chain even while conventional curved rails are used as they are, and can achieve structural simplicity through minimal components.

A further object of the present invention is to provide a method of using the chain stabilizing device which can fundamentally solve the phenomenon of extension of a chain during use of a hyperthermo-therapeutic apparatus and allow use of existing curved rails conforming to the shape of a user's body.

Technical Solution

The present invention relates to a chain stabilizing device in a hyperthermo-therapeutic apparatus, a hyperthermo-therapeutic apparatus mounted with the chain stabilizing device, and a method of using the chain stabilizing device. In order to achieve these objects, the present invention is to provide an apparatus for stabilizing a chain in a hyperthermo-therapeutic apparatus, comprising a chain stabilization control unit for stably moving the chain at a constant level regardless of an upward/downward movement of a hyperthermo-therapeutic unit of the hyperthermo-therapeutic apparatus during forward/backward reciprocation of the hyperthermo-therapeutic unit; and a chain-tension control unit for adjusting a tension on the chain, which can be generated during the forward and backward reciprocation of the hyperthermo-therapeutic unit.

In the present invention, the chain stabilization control unit may comprise a) a first hinge shaft having rotatable rollers provided at both side ends thereof, and chain-coupling sections provided at both sides of a central portion thereof; b) level control rods each of which has one end hingedly coupled to the first hinge shaft and the other end hingedly coupled to a second hinge shaft; c) the second hinge shaft being hingedly coupled to the other ends of the level control rods and simultaneously to a lower end of a central portion of a hyperthermo-therapeutic unit support; and d) the hyperthermo-therapeutic unit support having a body section with the hyperthermo-therapeutic unit mounted thereon, the hyperthermo-therapeutic unit support having the lower end of the central portion thereof hingedly coupled to the second hinge shaft and having rotatable rollers coupled to both side ends thereof.

In the present invention, the rollers may be engaged with linear rails mounted inside a mat of the hyperthermo-therapeutic apparatus. In order to enable the rollers to be stably moved in the linear rails and to prevent the rollers from coming off from the rails in a case where the hyperthermo-therapeutic apparatus is loaded in an inverted state during transportation of the hyperthermo-therapeutic apparatus, it is preferred that the linear rails be manufactured into 90°-rotated U-shaped dual rails.

In the present invention, the level control rods preferably have upper ends of which levels are changed by changing angles of the rods in such a manner that lower ends thereof can pivot on the first hinge shaft according to the forward/backward movement of the first hinge shaft.

In the present invention, the chain-tension control unit preferably comprises a free pulley located at a side opposite to the electric motor and rotated freely by the chain wrapped therearound; a level control pulley located above and in front of the free pulley so as to adjust a level of the chain to positions of the chain-coupling sections; a cover body section for protecting the free pulley and the level control pulley against external pressure; and a tension-adjusting means for adjusting the tension by moving the chain-tension control unit in a forward/backward direction with respect to the electric motor according to a condition of the tension on the chain.

A hyperthermo-therapeutic apparatus of the present invention comprises a main mat having an elongated groove formed at a central portion thereof and including a hyperthermo-therapeutic unit reciprocating in the elongated groove; rails formed at both sides of a lower portion of the central elongated groove of the main mat and serving as guiders for guiding the forward/backward reciprocation or upward/downward movement of the hyperthermo-therapeutic unit; a chain stabilization control unit for stably moving a chain at a constant level regardless of the upward/downward movement of the hyperthermo-therapeutic unit during the forward/backward reciprocation of the hyperthermo-therapeutic unit; a chain-tension control unit for adjusting a tension on the chain, which is generated during the forward/backward reciprocation of the hyperthermo-therapeutic unit; a feeding means including an electric motor for generating a force for use in reciprocating the hyperthermo-therapeutic unit, and the chain for transmitting the force of the electric motor to the hyperthermo-therapeutic unit; and a control panel for use in controlling the feeding means, and an operating panel for use in manipulating the location of the roller type hyperthermo-therapeutic unit.

It is preferred that the hyperthermo-therapeutic apparatus of the present invention further comprise an auxiliary mat electrically connected to the main mat so as to perform a hot compress on a lower part of a user's body.

Further, it is preferred that the hyperthermo-therapeutic apparatus of the present invention further comprise a frame body on which the main mat and the auxiliary mat can be mounted.

Moreover, the hyperthermo-therapeutic apparatus of the present invention can be used by a) moving a chain directly coupled to a first hinge shaft while constantly maintaining a level of the chain regardless of an upward/downward movement of the hyperthermo-therapeutic unit, by rollers installed at both side ends of the first hinge shaft and rotatably engaged with linear rails, during the forward/backward reciprocation of the hyperthermo-therapeutic unit, thereby ensuring stabilization of the chain; and b) if a tension on the chain is out of an initial adjusted tension range during the forward/backward reciprocation of the hyperthermo-therapeutic unit, shifting the position of the hyperthermo-therapeutic unit in a forward or backward direction with respect to an electric motor according to a condition of the tension on the chain, thereby adjusting the tension on the chain. Thus, the hyperthermo-therapeutic apparatus can be used in a more efficient and stable state obtained through the aforementioned processes.

Advantageous Effects

As described above, when the chain stabilization control unit of the hyperthermo-therapeutic apparatus according to the present invention is employed, there is an advantage in that since a tension exerted on the chain is always maintained constantly, there is no room for generation of a phenomenon of extension of the chain that may occur in a prior art.

Moreover, the chain stabilization control unit of the hyperthermo-therapeutic apparatus according to the present invention has an advantage in that it can be simply constructed of only minimal components by employing the first and second hinge shafts as main components and hingedly coupling the level control rods between the hinge shafts.

Furthermore, the chain stabilization control unit of the hyperthermo-therapeutic apparatus according to the present invention has additional advantages in that minimal raw materials are used to obtain a lightweight product and a load on the electric motor is reduced to prolong an average life span of the product.

In addition, since the chain stabilization control unit of the hyperthermo-therapeutic apparatus according to the present invention is provided with a means for adjusting a tension on the chain, there is an advantage in that a user can easily adjust the tension on the chain by simply operating the means from the outside of the device even though the tension on the chain is inevitably reduced due to use of the chain for a long time.

BEST MODE FOR CARRYING OUT THE INVENTION

Figure 1:
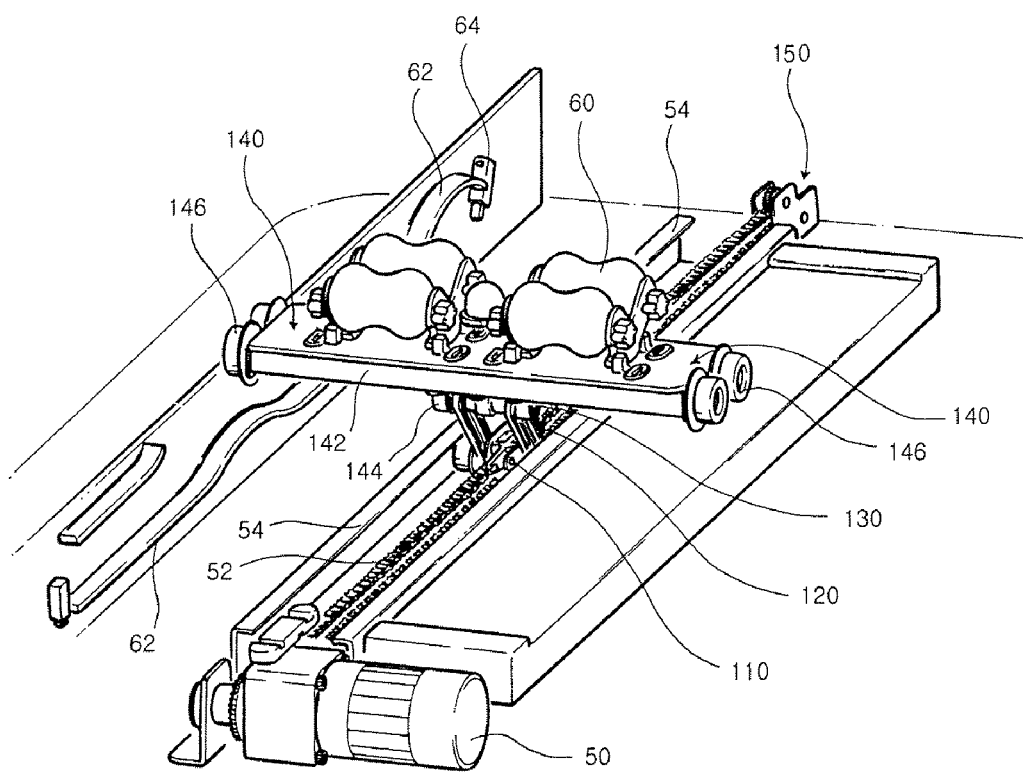
FIG. 1 is a schematic perspective view illustrating a chain stabilizing device in a hyperthermo-therapeutic apparatus according to the present invention.
Figure 2:
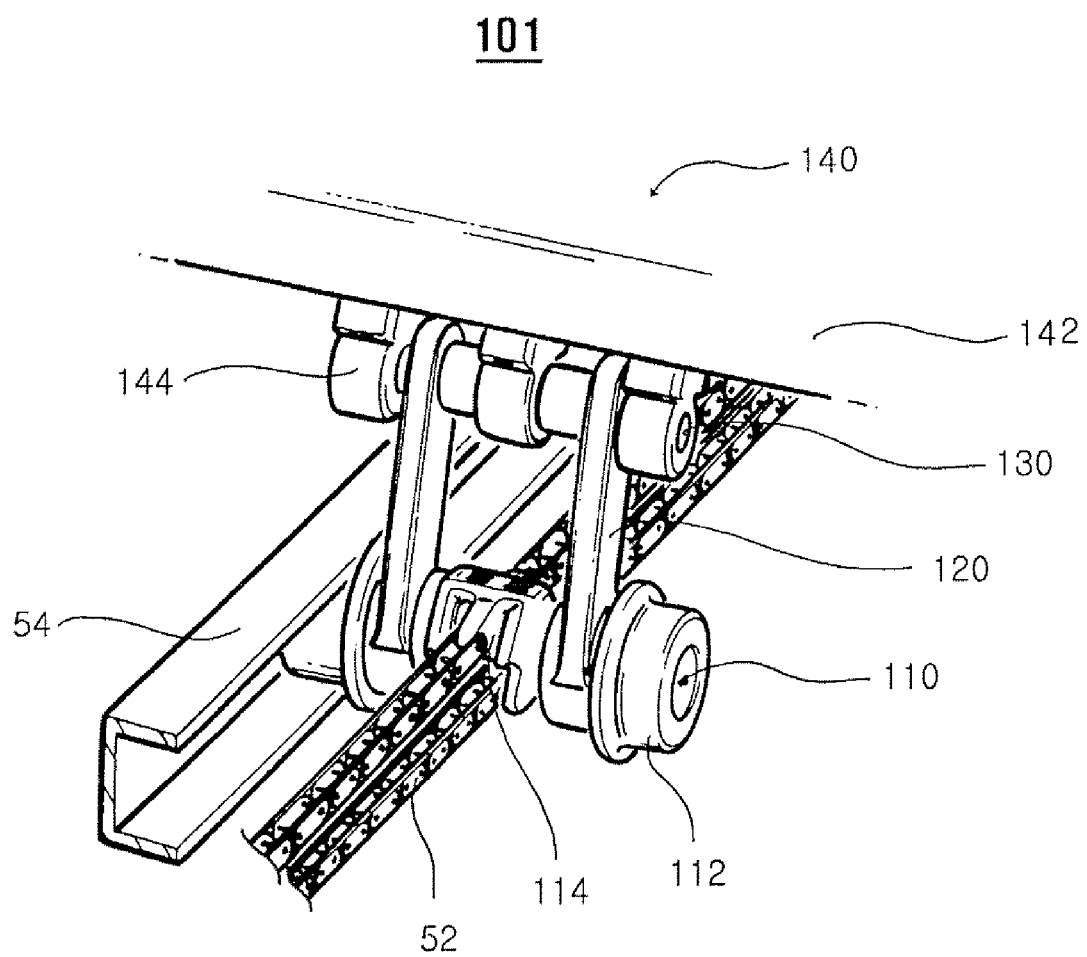
FIG. 2 is a schematic perspective view of major portions of the chain stabilizing device in the hyperthermo-therapeutic apparatus according to the present invention.

Hereinafter, the present invention will be described in greater detail with reference to accompanying drawings. However, it will be apparent that the accompanying drawings only illustrate the technical sprit of the present invention and the technical spirit of the present invention is not limited thereto.

A chain stabilizing device 100 in a hyperthermo-therapeutic apparatus according to the present invention comprises a chain stabilization control unit 101 for stably moving a chain 52 at a constant level regardless of upward/downward movement of a hyperthermo-therapeutic unit 60 during forward/backward reciprocation of the hyperthermo-therapeutic unit.

In the present invention, the chain stabilization control unit 101 comprises a first hinge shaft 110 that is moved in the forward/backward direction in response to an operation of an electric motor 50.

In the present invention, the first hinge shaft 110 has chain-coupling sections 114 provided at both sides of a central portion thereof, and a belt or the chain 52 is coupled to respectively front portion and rear portion of the chain stabilizing device through the chain-coupling sections 114. Accordingly, as the electric motor 50 is operated, the belt or the chain 52 coupled to the electric motor is moved in the forward/backward direction, and the first hinge shaft 110 coupled to the belt or the chain is also moved in the forward/backward direction in response to the movement of the belt or the chain 52.

Further, the first hinge shaft 110 has rotatable rollers 112 provided at both side ends thereof. The rollers 112 are engaged with linear rails 54 mounted at an inside portion of a mat of the hyperthermo-therapeutic apparatus, and are moved in the forward/backward direction while being rolled along the linear rails 54. At this time, in order to enable the rollers to be stably moved in the linear rails 54 and to prevent the rollers 112 from coming off from the rails in a case where the hyperthermo-therapeutic apparatus is loaded in an inverted state during transportation of the hyperthermo-therapeutic apparatus, it is preferred that the linear rails 54 be manufactured into 90°-rotated U-shaped dual rails.

In the present invention, the chain stabilization control unit 101 comprises level control rods 120 of which the level of upper ends are changed by changing the angles of the rods in such a manner that lower ends thereof can pivot on the first hinge shaft 110 according to the forward/backward movement of the first hinge shaft 110.

In the present invention, the level control rod 120 is characterized in that one end thereof is hingedly coupled to the first hinge shaft 110. Since one end of the level control rod 120 is directly and hingedly coupled to the first hinge shaft 110, the level control rod 120 is moved directly in response to the electric motor 50 when the electric motor is operated, thereby changing a final level of the level control rod and there is no need for provision of an additional hinge means at another position for achieving the above function. Accordingly, by directly and hingedly coupling one end of the level control rod 120 to the first hinge shaft 110, it is possible to achieve the maximum effects through the simplest structure.

In addition, in the present invention, the other end of the level control rod 120 is also directly and hingedly coupled to a second hinge shaft 130. As described above, this is to achieve the most efficient function even while employing the simplest structure.

In the present invention, the chain stabilization control unit 101 comprises the second hinge shaft 130 that is moved in the upward/downward direction in response to the varying levels of the level control rods 120. The other end of the level control rod 120 is hingedly coupled to the second hinge shaft 130. Accordingly, when the level of the upper end of the level control rod 120 is changed in the upward/downward direction, the second hinge shaft 130 can be smoothly moved in the upward/downward direction through the hinge coupling between the level control rod and the second hinge shaft. Simultaneously, the second hinge shaft 130 is hingedly coupled to a lower end of a central portion of a hyperthermo-therapeutic unit support 140. Due to this structure, when the second hinge shaft 130 is moved in the upward/downward direction, the hyperthermo-therapeutic unit support 140 can be moved in the upward/downward direction in response to the movement of the second hinge shaft.

In the present invention, the chain stabilization control unit 101 comprises the hyperthermo-therapeutic unit support 140 on which the hyperthermo-therapeutic unit 60 can be mounted.

In the present invention, the hyperthermo-therapeutic unit support 140 comprises a body section 142 at a central portion thereof, and the hyperthermo-therapeutic unit 60 can be mounted on the body section 142. The hyperthermo-therapeutic unit 60 provides a user with a hot compress effect, an acupressure effect and a radiation effect of far infrared rays. Further, the hyperthermo-therapeutic unit support 140 comprises hinge-coupling sections 144 provided at a central portion of a lower surface thereof, and the hinge-coupling sections 144 are directly and hingedly coupled to the level control rods 120 through the second hinge shaft 130. In the present invention, the reason why the hinge-coupling sections 144 are coupled to the central portion of the lower surface of the hyperthermo-therapeutic unit support 140 and then hingedly coupled to the level control rods 120 together with the second hinge shaft 130 is that the second hinge shaft is utilized as a central shaft for the hinge coupling so that its structural configuration can be minimized and it is possible to obtain structural simplicity and a maximized efficiency.

Moreover, in the present invention, the hyperthermo-therapeutic unit support 140 comprises rollers 146 provided at and rotatably coupled to both side ends thereof. The rollers 146 are engaged with curved rails 62 in contrast to the structure in which the rollers 112 coupled to the first hinge shaft 110 are engaged with the linear rail 54. Accordingly, the rollers 146 ensure smooth movement of the hyperthermo-therapeutic unit support 140 in the forward/backward directions and simultaneously provide the foundation enabling the hyperthermo-therapeutic unit support 140 to be moved smoothly in the upward/downward directions along the curved rails 62.

The chain stabilizing device 100 according to the present invention comprises a chain-tension control unit 150 capable of adjusting a tension on the chain 52, which is generated during the forward/backward reciprocation of the hyperthermo-therapeutic unit 60.

In the present invention, the chain-tension control unit 150 comprises a free pulley 152 located at a side opposite to the electric motor and rotated freely by the chain 52 wrapped therearound; and a level control pulley 154 located above and in front of the free pulley so as to adjust the level of the chain 52 to the positions of the chain-coupling sections 114. In the present invention, when the chain 52 is moved by the electric motor 50, the free pulley 152 provides a turning point of the chain, while the level control pulley 154 can constantly maintain the level of the chain 52.

In the present invention, the chain-tension control unit 150 comprises a cover body section 156 for protecting the free pulley 152 and the level control pulley 154 against external pressure.

Further, in the present invention, the chain-tension control unit 150 comprises a tension-adjusting means 158 that can adjust the tension by moving the chain-tension control unit in the forward/backward direction with respect to the electric motor 50 according to a condition of the tension on the chain 52. The tension-adjusting means 158 can consist of a bolt and a nut that can be adjusted to shift the actual position of the chain-tension control unit 150 forward or backward with respect to the electric motor 50, thereby adjusting the tension on the chain 52.

In addition, the present invention provides the hyperthermo-therapeutic apparatus 200 comprising the chain stabilizing device 100.

Figure 4:
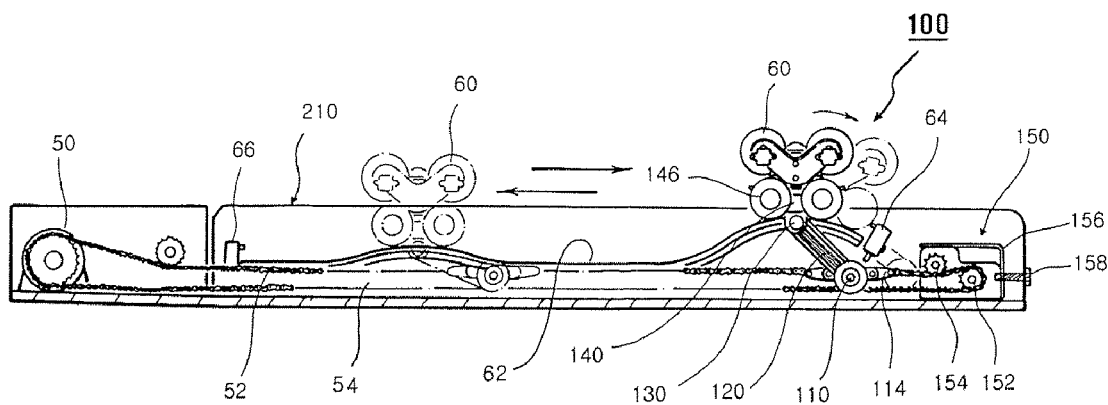
FIG. 4 is a schematic side view showing a use state of the chain stabilizing device in the hyperthermo-therapeutic apparatus according to the present invention.

FIG. 4 is a side sectional view schematically showing an operational relationship between the hyperthermo-therapeutic apparatus 200 and the chain stabilizing device 100, illustrating relationships among respective components mounted inside a main mat of the hyperthermo-therapeutic apparatus.

The hyperthermo-therapeutic apparatus 200 according to the present invention comprises the main mat 210 having an elongated groove formed at a central portion thereof and including the hyperthermo-therapeutic unit 60 that is reciprocated in the elongated groove. The main mat 210 is used for performing a hot compress on an upper part of a user's body when the user lies on the main mat. The main mat is a common component in a hyperthermo-therapeutic apparatus.

The hyperthermo-therapeutic apparatus 200 according to the present invention comprises rails that are formed at both sides of a lower portion of the central elongated groove of the main mat 210 and serve as guiders for guiding the forward/backward reciprocation or upward/downward movement of the hyperthermo-therapeutic unit 60. The rails comprise the linear rails 54 for guiding the linear reciprocation of the hyperthermo-therapeutic unit 60 and the curved rails 62 for guiding the vertical movement of the hyperthermo-therapeutic unit 60.

Further, the hyperthermo-therapeutic apparatus 200 according to the present invention comprises the chain stabilization control unit 101 which stably moves the chain 52 at a constant level regardless of the vertical movement of the hyperthermo-therapeutic unit 60 during the forward/backward reciprocation of the hyperthermo-therapeutic unit. Since the chain stabilization control unit 101 has been described above in detail, a repeated description thereof will be omitted herein.

Further, the hyperthermo-therapeutic apparatus 200 according to the present invention comprises the chain-tension control unit 150 capable of adjusting the tension on the chain 52, which is generated during the forward/backward reciprocation of the hyperthermo-therapeutic unit 60. Similarly, since the chain-tension control unit 150 has been described above in detail, a repeated description thereof will be omitted herein.

In addition, the hyperthermo-therapeutic apparatus 200 according to the present invention comprises a feeding means including the electric motor 50 for generating a force for use in reciprocating the hyperthermo-therapeutic unit 60, and the chain 52 for transmitting the force of the electric motor to the hyperthermo-therapeutic unit; a control panel (not shown) for use in controlling the feeding means; and an operating panel (not shown) for use in manipulating the location of the roller type hyperthermo-therapeutic unit. However, since these components are components generally used in a conventional hyperthermo-therapeutic apparatus, detailed descriptions thereof will be omitted herein.

The present invention constructed as above is operated as follows (see FIG. 4).

Figure 3:
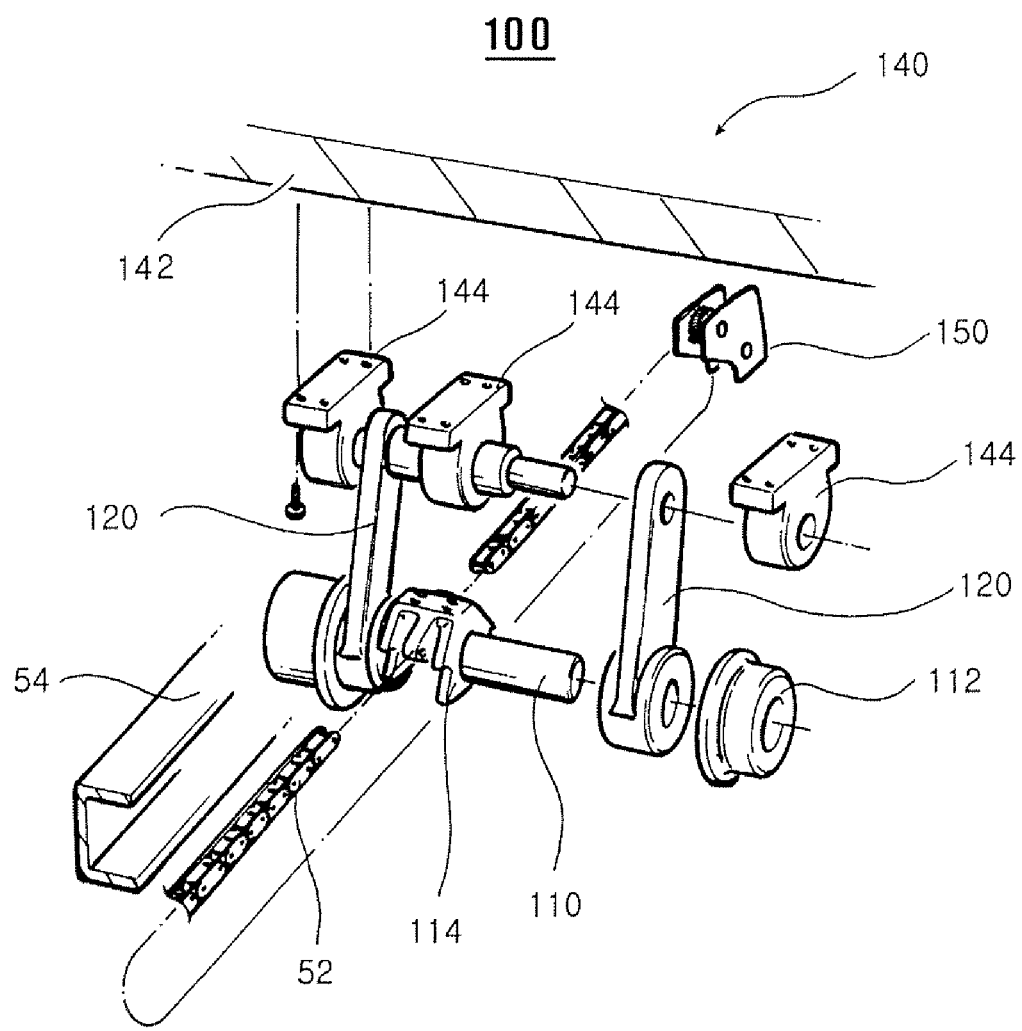
FIG. 3 is an exploded perspective view of the major portions shown in FIG. 2.

First of all, a description will be made in connection with a case where a user operates the electric motor 50 through a remote control (not shown) so that the chain stabilizing device 100 in the hyperthermo-therapeutic apparatus according to the present invention can be moved backward (in the right direction in FIG. 3).

When the user operates the electric motor 50, the chain 52 is pulled in the backward direction by the rotational force of the electric motor, and the chain 52 pulls the first hinge shaft 110 coupled thereto in the backward direction. At this time, since the rollers 112 coupled to the both side ends of the first hinge shaft 110 are rotatably engaged in the linear rails 54, the rollers are rolled while being rotated in the linear rails 54, so that the first hinge shaft 110 is linearly moved in the backward direction (in the right direction in FIG. 3).

Meanwhile, as the first hinge shaft 110 is pulled in the backward direction, a pulling force is transmitted to the level control rods 120 hingedly coupled to the first hinge shaft and then transmitted to the second hinge shaft 130 as it is. Further, this pulling force is transmitted to the hyperthermo-therapeutic unit support 140 coupled to the second hinge shaft. Accordingly, as the electric motor 50 is operated, the hyperthermo-therapeutic unit support 140 is moved entirely in the backward direction as a whole in response to the operation of the electric motor.

At this time, however, since the hyperthermo-therapeutic unit 60 mounted on the hyperthermo-therapeutic unit support 140 supports vertebral regions of the user who lies over the hyperthermo-therapeutic unit, a downward force is naturally exerted on the hyperthermo-therapeutic unit support 140.

In this state, when the first hinge shaft 110 reaches curved portions of the curved rails 62, the rollers 146 coupled to the both side ends of the hyperthermo-therapeutic unit support 140 are moved upward along the curved portions of the curved rails 62. At the same time, the hyperthermo-therapeutic unit support 140 is moved upward, so that the hyperthermo-therapeutic unit 60 mounted thereon can be simultaneously moved upward. When the electric motor 50 is further driven, the rollers 146 have passed the curved portions of the curved rails 62 and then reach declined portions of the curved rails. Accordingly the hyperthermo-therapeutic unit 60 begins to gradually move downward. However, when the electric motor 50 is further driven, the rollers 146 pushes a switch 64 for converting the rotational direction of the motor. Therefore, the converting switch 64 converts the rotational direction of the electric motor 50 in an opposite direction.

Subsequently, in response to the conversion of the rotational direction of the electric motor 50 into the opposite direction, the movement direction of the chain stabilizing device 100 in the hyperthermo-therapeutic apparatus according to the present invention is also converted and advanced toward the electric motor 50 (in the left direction in FIG. 3).

In this case, the chain 52 is pulled toward the electric motor 50, and the pulling force is transmitted directly to the level control rods 120, so that the level control rods 120 are pushed forward and continue to advance while downward moving the hyperthermo-therapeutic unit support 140 coupled hingedly thereto. Thereafter, when the level control rods have passed again the linear portions and reach the curved portions of the curved rails 62, the level control rods raise the hyperthermo-therapeutic unit support 140 and continue to advance toward the electric motor 50. Finally, the advance direction of the level control rods is converted by a switch 66 for converting the rotational direction of the motor.

In this process, according to the forward/reverse rotation of the electric motor 50, the hyperthermo-therapeutic unit support 140 and the hyperthermo-therapeutic unit 60 mounted thereon are reciprocated in the forward/backward direction and also moved in the upward/downward direction depending on the curved portions of the curved rails 62. This can also be done in a case where conventional curved rails are used as they are.

On the contrary, even though the electric motor 50 is driven in the forward and reverse directions, the first hinge shaft 110 is reciprocated only in a linear manner by the rollers 112 rotatably coupled to the linear rails 54, without any vertical movement. Accordingly, even though the hyperthermo-therapeutic unit 60 is reciprocated in the forward/backward direction, the chain 52 coupled directly to the first hinge shaft 110 is subjected to a tension in a linear direction. Thus, the chain is always subjected to only a uniform tension.

Meanwhile, if the chain 52 is extended and has a reduced tension due to user's use of the hyperthermo-therapeutic apparatus for a long time or a user intends to slightly reduce the tension on the chain, it is sufficient to simply manipulate the chain-tension control unit 150. For example, the user can adjust the tension on the chain 52 by fastening or releasing the tension-adjusting means 158 capable of forward or backward shifting the position of the tension control unit with respect to the electric motor according to a condition of the tension on the chain 52.

INDUSTRIAL APPLICABILITY

Since the chain stabilizing device in the hyperthermo-therapeutic apparatus according to the present invention employs only minimal components as essential components, it is possible to save raw materials, simplify an assembling process of a product, and significantly reduce a possibility of occurrence of a failure even though the apparatus is utilized for a long time.

Although the chain stabilizing device in the hyperthermo-therapeutic apparatus according to the present invention has been described above, it is intended to illustrate the most preferred embodiment of the present invention. The present invention is not limited thereto and the scope of the invention is determined and defined only by the appended claims.

Further, it will be apparent that those skilled in the art can make various changes and modifications thereto from the disclosure herein, and the various changes and modifications fall within the scope of the invention.

The invention claimed is:

1. A device for stabilizing a chain in a hyperthermo-therapeutic apparatus, the device comprising:
  a chain stabilization control unit for stably moving the chain at a constant level regardless of an upward/downward movement of a hyperthermo-therapeutic unit of the hyperthermo-therapeutic apparatus during forward/backward reciprocation of the hyperthermo-therapeutic unit, the chain stabilization control unit comprising:
  a first hinge shaft having rotatable rollers provided at both side ends of the first hinge shaft and chain-coupling sections provided at both sides of a central portion of the first hinge shaft,
  level control rods, each of the level control rods having one end hingedly coupled to the first hinge shaft and the other end hingedly coupled to a second hinge shaft,
  the second hinge shaft being hingedly coupled to the other ends of the level control rods and simultaneously to a lower end of a central portion of a hyperthermo-therapeutic unit support, and
  the hyperthermo-therapeutic unit support having a body section that mounts the hyperthermo-therapeutic unit, the hyperthermo-therapeutic unit support having the lower end of the central portion of the hyperthermo-therapeutic unit support hingedly coupled to the second hinge shaft and having rotatable rollers coupled to both side ends of the hyperthermo-therapeutic unit support, and
  wherein the first hinge shaft, the second hinge shaft, and control rods generally lie within a common plane as the first hinge shaft moves forwards and backwards; and
  a chain-tension control unit for adjusting a tension on the chain, which is configured to be generated during the forward and backward reciprocation of the hyperthermo-therapeutic unit.

2. The device as claimed in claim 1, wherein the chain-tension control unit comprises:
  a free pulley located at a side opposite to the electric motor and rotated freely by the chain wrapped therearound;
  a level control pulley located above and in front of the free pulley so as to adjust a level of the chain to positions of the chain-coupling sections;
  a cover body section for protecting the free pulley and the level control pulley against external pressure; and
  a tension-adjuster for adjusting the tension by moving the chain-tension control unit in a forward/backward direction with respect to the electric motor according to a condition of the tension on the chain.

3. The device as claimed in claim 1, wherein the level control rods have upper ends of which levels are changed by changing angles of the rods in such a manner that lower ends thereof can pivot on the first hinge shaft according to the forward/backward movement of the first hinge shaft.

4. A hyperthermo-therapeutic apparatus for providing a user with hot compress and massage effects, the hyperthermo-therapeutic apparatus comprising:
  a main mat having an elongated groove formed at a central portion of the main mat and including a hyperthermo-therapeutic unit reciprocating in the elongated groove;
  linear rails and curves rails formed at both sides of a lower portion of the central elongated groove of the main mat and serving as guiders for guiding the forward/backward reciprocation or upward/downward movement of the hyperthermo-therapeutic unit;
  a chain stabilization control unit for stably moving a chain at a constant level regardless of the upward/downward movement of the hyperthermo-therapeutic unit during the forward/backward reciprocation of the hyperthermo-therapeutic unit, the chain stabilization control unit comprising:
  a first hinge shaft having rotatable rollers provided at both side ends of the first hinge shaft and chain-coupling sections provided at both sides of a central portion of the first hinge shaft,
  level control rods, each of the level control rods having one end hingedly coupled to the first hinge shaft and the other end hingedly coupled to a second hinge shaft,
  the second hinge shaft-being hingedly coupled to the other ends of the level control rods and simultaneously to a lower end of a central portion of a hyperthermo-therapeutic unit support, and
  the hyperthermo-therapeutic unit support having a body section that mounts the hyperthermo-therapeutic unit, the hyperthermo-therapeutic unit support having the lower end of the central portion of the hyperthermo-therapeutic unit support hingedly coupled to the second hinge shaft and having rotatable rollers coupled to both side ends of the hyperthermo-therapeutic unit support, and
  wherein the first hinge shaft, the second hinge shaft, and control rods generally lie within a common plane as the first hinge shaft moves forwards and backwards along the linear rails;
  a chain-tension control unit for adjusting a tension on the chain, which is generated during the forward/backward reciprocation of the hyperthermo-therapeutic unit;
  a feeder including an electric motor for generating a force for use in reciprocating the hyperthermo-therapeutic unit, and the chain for transmitting the force of the electric motor to the hyperthermo-therapeutic unit; and
  a control panel for use in controlling the feeder, and an operating panel for use in manipulating the location of the roller type hyperthermo-therapeutic unit.

5. The apparatus as claimed in claim 4, wherein the chain-tension control unit comprises:
  a free pulley located at a side opposite to the electric motor and rotated freely by the chain wrapped therearound;
  a level control pulley located above and in front of the free pulley so as to adjust a level of the chain to positions of the chain-coupling sections;
  a cover body section for protecting the free pulley and the level control pulley against external pressure; and
  a tension-adjuster for adjusting the tension by moving the chain-tension control unit in a forward/backward direction with respect to the electric motor according to a condition of the tension on the chain.

6. A method of using a hyperthermo-therapeutic apparatus for performing a hot compress on a user by reciprocating a hyperthermo-therapeutic unit in a forward/backward direction, the method comprising:

moving a chain directly coupled to a first hinge shaft while constantly maintaining a level of the chain regardless of an upward/downward movement of the hyperthermo-therapeutic unit, by rollers installed at both side ends of the first hinge shaft and rotatably engaged with linear rails, during the forward/backward reciprocation of the hyperthermo-therapeutic unit, thereby ensuring stabilization of the chain, providing the first hinge shaft with chain-coupling sections provided at both sides of a central portion of the first hinge shaft, providing level control rods, each of the level control rods having one end hingedly coupled to the first hinge shaft and the other end hingedly coupled to a second hinge shaft, providing the second hinge shaft to be hingedly coupled to the other ends of the level control rods and simultaneously to a lower end of a central portion of a hyperthermo-therapeutic unit support, and providing the hyperthermo-therapeutic unit support with a body section that mounts the hyperthermo-therapeutic unit, the hyperthermo-therapeutic unit support having the lower end of the central portion thereof hingedly coupled to the second hinge shaft and having rotatable rollers coupled to both side ends of the hyperthermo-therapeutic unit support, and wherein the first hinge shaft, the second hinge shaft, and control rods generally lie within a common plane as the first hinge shaft moves forwards and backwards along the linear rails;

when a tension on the chain is out of an initial adjusted tension range during the forward/backward reciprocation of the hyperthermo-therapeutic unit, shifting the position of the hyperthermo-therapeutic unit in a forward or backward direction with respect to an electric motor according to a condition of the tension on the chain, thereby adjusting the tension on the chain; and using the hyperthermo-therapeutic apparatus in a stable state obtained by stabilizing the chain and adjusting the tension on the chain.

\* \* \* \* \*